(12) United States Patent
Rubinfeld

(10) Patent No.: US 11,751,761 B1
(45) Date of Patent: Sep. 12, 2023

(54) SYSTEM AND METHOD FOR CALCULATING BINOCULAR ALIGNMENT

(71) Applicant: Eric Rubinfeld, Yonkers, NY (US)

(72) Inventor: Eric Rubinfeld, Yonkers, NY (US)

(*) Notice: Subject to any disclaimer, the term of this patent is extended or adjusted under 35 U.S.C. 154(b) by 0 days.

(21) Appl. No.: 18/147,122

(22) Filed: Dec. 28, 2022

(51) Int. Cl.
*A61B 3/08* (2006.01)
*A61B 3/113* (2006.01)
*A61B 3/00* (2006.01)

(52) U.S. Cl.
CPC .............. *A61B 3/08* (2013.01); *A61B 3/005* (2013.01); *A61B 3/113* (2013.01)

(58) Field of Classification Search
CPC ..... A61B 3/028; A61B 3/0041; A61B 3/0033; A61B 3/0025; A61B 3/0083; G06K 9/6215

USPC ........................................................ 351/222
See application file for complete search history.

(56) References Cited

U.S. PATENT DOCUMENTS

| | | | | |
|---|---|---|---|---|
| 10,952,605 | B1* | 3/2021 | Rubinfeld | A61B 3/0083 |
| 2017/0295362 | A1* | 10/2017 | Travis | H04N 13/128 |
| 2018/0035102 | A1* | 2/2018 | Juenger | H04N 13/327 |
| 2021/0290053 | A1* | 9/2021 | Tran | A61B 3/10 |

* cited by examiner

*Primary Examiner* — Mohammed A Hasan
(74) *Attorney, Agent, or Firm* — RC Trademark Company

(57) ABSTRACT

According to some embodiments, a system and method for calculating binocular alignment is disclosed. The system and method comprise and utilize a first computing device for displaying different images for a first eye associated with a patient and a second eye associated with the patient. The first computing device is worn by the patient. A second computing device is used to determine a position of the first eye and the second eye.

9 Claims, 3 Drawing Sheets

200

Initiating a binocular alignment test on a first computing device;
210

Linking a program on a second computing device with the binocular alignment test on the first computing device
220

Tracking a gaze direction of a first eye of a patient and a gaze direction of a second eye of a patient
230

Calculating the binocular alignment at the second computing device
240

SYSTEM AND METHOD FOR CALCULATING BINOCULAR ALIGNMENT

BACKGROUND

Pathogens, such as the novel coronavirus (COVID-19) may be spread through aerosols and respiratory droplets that are expelled from a person's mouth or nose when an infected person talks, coughs or sneezes. Because of the rapid spread of COVID-19, people are avoiding crowded areas or areas where people congregate. Eye exams are just one example of where people may have to wait for long periods of time in a crowded room. One such eye exam is a test for binocular vision which is the process by which the brain integrates information from a person's two eyes to generate one clear unified image. A patient that suffers from binocular vision dysfunction may experience reading or learning difficulties, attention or concentration issues, double vision, headaches or eyestrain as well as other issues.

Therefore, a system to remotely determine eye alignment related to binocular vision dysfunction so that the patient may avoid contracting COVID-19 is desirable.

SUMMARY

Some embodiments described herein relate to a system and method of calculating binocular alignment. The system comprises a first computing device and a second computing device. The first computing device displays different images for (i) a first eye associated with a patient and (ii) a second eye associated with the patient. The first computing device is worn by the patient. The second computing device determines a position of the first eye and the second eye.

DETAILED DESCRIPTION

Figure 1:
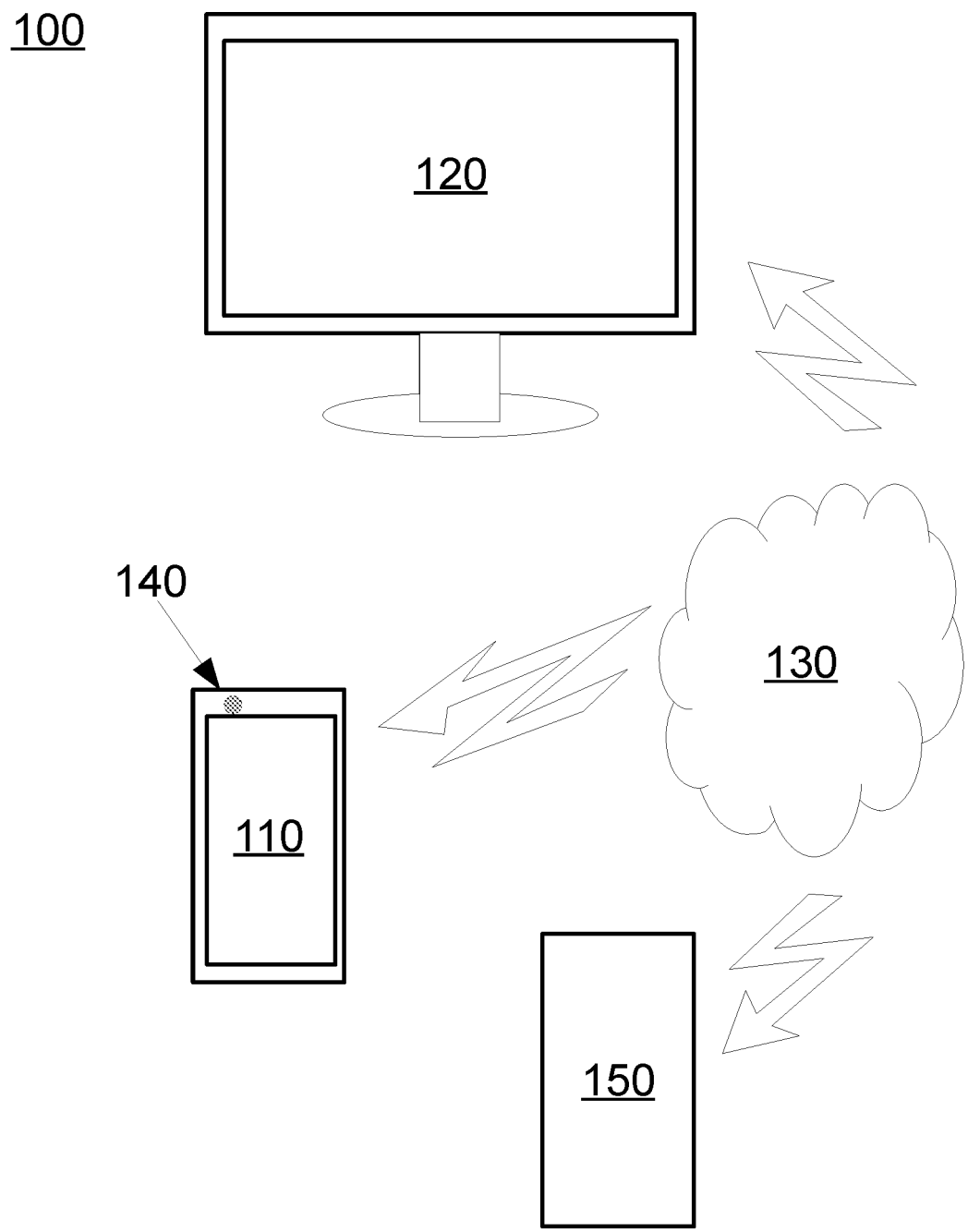
FIG. 1 illustrates a system for calculating binocular alignment in accordance with some embodiments.

In the following detailed description, numerous specific details are set forth in order to provide a thorough understanding of the embodiments. However, it will be understood by those of ordinary skill in the art that the embodiments may be practiced without these specific details. In other instances, well-known methods, procedures, components and circuits have not been described in detail so as not to obscure the embodiments.

In our proposed patent for binocular testing, when the distance between the images seen in each is increased, then the projections into the two eyes start to differ and become difficult to fuse. At some distance between the viewed objects the discrepancy between the visual perceptions of the two eyes exceeds a threshold, and the brain stops fusing the two images into a single perception and the patient perceives double vision. These measurements are quantifiable in our system with known variables (pupillary distance, distance from target, distance separation between the 2 independent images seen in each eye). The angle corresponding to visual axes (the line of site that runs through the middle of each pupil to the image or target) and the dissociation of binocularity when the target images can no longer be fused is referred to as an associated phoria. Adjustable prisms are in the VR headset and in front of the patient's eyes. These prisms are adjusted until the two images are perceived as aligned by the patient. Then the prism angles (or visual axes) are reported as the associated phoria.

Eyes have six muscles, which are responsible for controlling the movement of the eyeballs (moving them up, down, left right, etc.). These six muscles are connected to the outside of the eyeball and are connected to specifically to the sclera (the white of the eye). The muscles (e.g., extraocular eye muscles) are amongst the fastest contracting, precisely controlled skeletal muscles in the human body and function as agonist and antagonist pairs to move the eyeball in different directions: 1. Superior and Inferior Rectus muscles. 2. Lateral and Medial Rectus muscles, and 3. Superior and Inferior Oblique muscle. Collectively, all the extraocular muscles form a complex relationship that allows for both fast (saccadic) and slow (pursuit) eye movements. A way to describe saccadic is that of a prehistoric man seeing movement in their periphery and they can quickly move their eyes in the direction of a potential danger. With pursuits, think prehistoric man locking onto the threat and tracking the threat as it moves across their path at different distances, away from them or towards them. The coordination of both eyes using the extraocular muscles is what gives us binocular vision which gives us a seamless view of the world.

For a modern man, visual demands are far removed from hunting to survive. Today, we have extensive near vision demands with the increased use of computers and mobile devices. In fact, since the pandemic began, computer/mobile device use has surged as has the increase in symptoms from what is now referred to as digital eye strain. These symptoms can include headaches, neck and shoulder pain, and eye irritation When there is an imbalance or misalignment between the visual feedback and our eyes, the result is over-stimulation. Ocular misalignments can occur when the following situations occur: (i) the eyes do not coordinate together with saccadic and/or pursuit eye movements. (ii) the eyes do not fuse (converge or diverge) uniformly causing a mismatch in function and vision between the eyes, (iii) the eyes drift apart (converge or diverge) after prolonged fusion (i.e., reading, tracking), and/or (iv) the eyes focus fluctuates (blurry/clear) when trying to fuse/read.

Most ocular misalignments may be subtle and may worsen as the digital near task time increases. The patients do not lose their binocular vision but as the task time increases, the effort to try and maintain their fusion and coordinate the eyes becomes difficult and starts to break down. As the demand on the visual system increases, the patient has to over compensate for the misalignments in order to maintain good binocular vision.

The reasons the link between visual misalignment and digital eyestrain has not been properly addressed by eyecare providers is that there were not obvious ocular misalignments (strabismus where by one or both eyes break fusion, one eye turns out/in/up or down). The signs of symptoms of digital eyestrain do not necessarily result in a loss of binocular vision and the ensuing symptoms are not typically linked to the task causing the symptoms because binocularity is maintained. The underlying cause of digital eyestrain is the effort the patient has to exert to maintain their binocular vision when fusing, reading and doing the task at hand. Measuring the patient's binocular vision effectively, in their natural body position has also not been an option to date. Testing behind an instrument not in free space cannot, and does not, simulate the patient's real-world situation that elicits their symptoms.

The Rectus muscle's primary function is to move the eyeballs in the four cardinal directions: up, down, left and right. The Oblique muscle's purpose is to stabilize the eyes by making micro adjustments to counter head, neck and body movement so as to stabilize the vision.

With normal vision, a person is typically able to focus and fuse on objects at both far and near. As stated previously, the optical system of the eye uses six extraocular muscles to change the focus between the different distances. These muscles adjust various positions of the eye when transitioning between distance and near targets. These extraocular muscle adjustments are neurologically synced to the muscles inside the eye that changes the shape of the crystalline lens thereby changing the focus (ciliary muscle) and the pupil size (iris dilator and sphincter muscle) so that the proper lighting is allowed into the eye (e.g., like the aperture of a camera) so that the image being targets is brought into focus based on the triangulation feedback from the muscles. Collectively, adjustment of the shape of the crystalline lens, pupil size and rotation of the eyeballs combine to give a person binocular vision.

To address the above-described medical need, the embodiments described herein include a method to determine binocular alignment that comprises measuring a disassociated phoria of a first eye and a second eye of a patient at a measured distance. An accommodative convergence of the first eye and the second eye at the measured distance is determined using the measured disassociated phoria.

The present embodiments described herein relate to a novel system and method of calculating binocular alignment that may be conducted away from an eye doctor's office to avoid contracting COVID-19. In particular, the present embodiments relate to a system that uses (1) a portable platform worn by the patient for displaying different images at real distances for (i) a first eye associated with a patient and (ii) a second eye associated with the patient and (2) a second computing device to display images/targets for the first computing device and to determine a position of the first eye and the second eye.

In conventional systems, the patient either has to describe what they are seeing (e.g., verbal input from the patient) or the patient is placed behind a machine that displays images using simulated distances (e.g., virtual reality) and the patient is sitting in non-normal (e.g., in a position that the patient would not be in outside of the doctor's office) such that the patient can interface with the machine.

The system and method described herein automatically measures the following binocular functions without requiring the verbal input from the patient and allowing the patient to remain in a normal seated or standing position. The system described herein measures oculomotor (pursuits and saccades), fusional ranges (limits of the eyes converging and diverging while maintaining binocular vision, phorias (the eyes position relative to each other while at rest with no visual demand), motor fields, fixation disparities (micro misalignments), and/or stereopsis (depth perception). In some embodiments, the system may make the aforementioned measurements based on pupillary distances ("PD") that measures the distances between pupils and the alignment of the pupils. The system described herein is used for determining a binocular alignment where the system comprises a stereo display whose images are projected on each eye. The system further comprises an eye tracker, to track an orientation of the first eye and the second eye. In some embodiments, the stereo display and the eye tracker are included in a wearable headset (e.g., a virtual reality headset). In some embodiments, computer may be coupled to a display screen (e.g., a virtual reality headset display) that houses the eye tracker for managing and determining the binocular alignment.

For binocular testing as described herein, when the distance between the images seen in each is either decreased or increased, then the projections into the two eyes start to differ and become difficult to fuse. At some distance between the viewed objects the discrepancy between the visual perceptions of the two eyes exceeds a threshold, and the brain stops fusing the two images into a single perception and the patient perceives double vision. These measurements are quantifiable in with known variables (pupillary distance, distance from target, distance separation between the 2 independent images seen in each eye). The angle corresponding to visual axes (the line of site that runs through the middle of each pupil to the image or target) and the dissociation of binocularity when the target images can no longer be fused is referred to as an associated phoria. Determining the prismatic power that optimally compensates binocular misalignments in real space is the pressing medical need being addressed with this device.

To test, each eye receives or views a projection of the same image from a remote computer that creates a fusible stimuli giving the illusion of binocular (3D) vision. This fused image is then manipulated to give the illusion of moving closer, further so as to measure the range of binocular vision, fixation disparity and phorias. The measuring of the range of fusion, fixation disparity and phorias can be conducted at different real distances. For example, the distance may comprise 20 feet (this is considered optical infinity), 24 inches (a typical computer distance) and 16 inches (a typical reading distance) while the patient is standing (e.g., a 20 foot target) or sitting (e.g., 24 and 16 inch target) in their natural position wearing a Virtual Reality (VR) headset that is paired with a computer system/monitor or other digital device. Measuring in this manor may obtain real world data in the patient's natural living/work environment.

Targets (e.g., virtual reality images) of varying size, detail and retinal disparity are presented to manage various vergence exercises. The targets may be created using virtual reality technology. The patient may wear a virtual reality headset that incorporates independent eye tracking and allows a doctor (or computer) to independently determine the position of both eyes at all times allowing the doctor (or computer) to assess the binocular vision of the patient. In use, virtual reality images/targets of varying size, detail and retinal disparity are presented to manage various vergence exercises. The virtual reality headset incorporates independent eye tracking to allows medical professionals to independently determine the position of both eyes at all times as well as allowing medical professionals to assess the binocular vision of the patient. Adjustable prisms may be in the virtual reality headset and in front of the patient's eyes. These prisms may be adjusted until the two images are perceived as aligned by the patient. Then the prism angles (or visual axes) are reported as the associated phoria.

Determining the prismatic power that optimally compensates binocular misalignments in real space may be a pressing medical need being addressed with the embodiments described herein.

Now referring to FIG. 1, an embodiment of a binocular alignment calculation system 100 is illustrated. As illustrated in FIG. 1, a first computing device 110 and a second computing device 120 may be communicatively coupled to a communication network 130. The communication network 130 may comprise any wired or wireless communication network that may be used for communication purposes between electronic devices. For example, the network 130 may comprise, but is not limited to, a wired and/or wireless mesh network, LAN, MAN, WAN, or the Internet.

For purposes of illustration, the second computing device 120 may comprise a desktop computer, a laptop or a tablet. The second computing device 120 may function as a image display device, a distance measuring device and a test calculation platform for administering a binocular alignment calculation test. The first computing device 110 may comprise a mobile device such as virtual reality headset/goggles, goggles with a display screen or a cardboard virtual reality headset that receives a smartphone to function as a display screen. In some embodiments, the first computing device 110 may function as a portable platform for displaying different images for (i) a first eye associated with a patient and (ii) a second eye associated with the patient at a predetermined distance from the second computing device 120.

The second computing device 120 may comprise a desktop computer, a laptop or a tablet that displays an image. In this embodiment, the first computing device 110 may comprise a wearable mobile device that displays images (e.g., holographic images) to each of the patient's eyes based on the image displayed on the second computing device 120. In some embodiments, the first computing device 110 may alternate between a first eye and a second eye based on being synchronized with a monitor associated with the second computing device 120. The second computing device 120 may function as a display device as well as a test calculation platform for administering a binocular alignment calculation test. The first computing device 110 may comprise a wearable mobile device that is synchronized to the second computing device 120 for measuring characteristics of the patient's eyes as the patient views a display screen associated with the second computing device 120 at real distances. The advantage of measuring characteristics of the patient's eyes at real distances is that the doctor can better understand the true issues that the patient is having because the patient is at true distances and is in a sitting/standing position that is normal for the patient. This is unlike the conventional prior art where the patient is not in a normal position and is not viewing images at real distances.

In some embodiments, the second computing device 120 may not allow for the test to be performed if the patient is not at, or greater than, a predetermined distance away from the first computing device 110. In some embodiments, the second computing device 120 may not start, or continue, a binocular alignment calculation if the patient is not at a predetermined distance away from the first computing device 110.

To determine distance, the first computing device 110 may include a measuring device 140 such as, but not limited to, a GPS radio, a WIFI radio, a camera and/or an augmented reality laser pointer. The measuring device 140 of the first computing device 110 may be in communication with the second computing device 120 to determine when a test should start or continue. The aforementioned measuring device 140 may be used for determining a distance from the first computing device 110 to the second computing device 120. In some embodiments, the first computing device 110 and the second computing device 120 may communicate with a back-end or remote server 150 via the communication network 130 as will be explained with respect to FIG. 2.

Figure 2:
FIG. 2 illustrates a method in accordance with some embodiments.
Figure 2:
Figure 2:

Now referring to FIG. 2, a method 200 that might be performed by the binocular alignment calculation system described with respect to FIG. 1 is illustrated according to some embodiments. The method described herein does not imply a fixed order to the steps, and embodiments of the present invention may be practiced in any order that is practicable. Note that any of the methods described herein may be performed by hardware, software, or any combination of these approaches. For example, a non-transitory computer-readable storage medium may store thereon instructions that when executed by a machine result in performance according to any of the embodiments described herein.

Method 200 may relate to calculating a binocular alignment calculation while a patient is remotely located from an eye doctors' office such as, but not limited to, at home. One of the main issues of calculating binocular alignment at home may be ensuring that the patient is taking the test at a required real distance away from a viewing platform because if the patient stands too close to the viewing platform, the binocular alignment calculation may not be accurate.

Now referring to 210, a binocular alignment calculation may be initiated on a second computing device. As stated previously, the second computing device may comprise, but is not limited to, a desktop, laptop or tablet computer. The second computing device may be used as a stationary viewing platform and a patient may view images using the first computing device from a predetermined distance away from the second computing device.

For purposes of illustrating features of the present embodiments, an example will now be introduced and referenced throughout the disclosure. Those skilled in the art will recognize that this example is illustrative and is not limiting and is provided purely for explanatory purposes. In some embodiments, a patient needs a binocular alignment calculation in response to being diagnosed with binocular vision dysfunction. Instead of having the test performed at their eye doctor's office, the patient may log into an online binocular alignment calculation system and start a binocular alignment calculation procedure using a headset that was sent to them via their doctor. The procedure may be hosted by a remote server that is in communication with the second computing device. The procedure may start by first linking a program on the second computing device with the binocular alignment test on the first computing device at 220.

Linking the program on a second computing device with the binocular alignment test on the first computing device, may comprise a Bluetooth (e.g., short-range wireless network connection), entering a phone number of the first computing device (e.g., a mobile device) so that a text message may be sent to the first or second computing device from the remote sever with a link such as a unique URL for the patient having his/her binocular alignment calculated. In this case, the patient can login to the binocular alignment calculation system using the link provided in the text message. In some embodiments, login identification may be displayed on the first computing device or the second computing device so that a patient may enter the login information into a web browser or other software to synchronize the second computing device with the first computing device. In some embodiments, linking may be based on viewing an image on the second computing device via the first computing device. For example, the image may comprise a bar code displayed on the second computing device that once viewed from the first computing devices, links the first computing device to the second computing device.

Since the second computing device may comprise a variety of screen sizes (e.g., ranging from 10" diagonal to 32" diagonal), a display on a screen associated with the second computing device may be calibrated prior to starting the binocular alignment calculation. Calibration may comprise adjusting a shape on the screen associated with the first computing device to match a size of a corresponding reference shape. For example, a patient may use a physical object such as a 4"×6" rectangle or another shaped object (e.g., a credit card). In some embodiments, a slider, or other type of adjustment control, may be used to change the size of the rectangle on the screen so that it matches the patient's object. Once the size of the screen matches the physical object, the patient may select a calibration button to indicate that the display on the first computing device has been calibrated.

Next, at 230, a gaze direction of a first eye of a patient is tracked and a gaze direction of a second eye of a patient is tracked. Tracking the gaze direction of each eye may be used to determine a binocular horizontal, pure symmetric vergence along the patient's egocentric midline. Tracking the gaze direction may be accomplished by displaying one or more targets (e.g., images) on the display associated with the second computing device. The targets may be displaced in depth at real physical distances at the first computing device. In some embodiments, the first computing device may use augmented reality to display or enhance/manipulate the images. Viewing the targets/images through the first computing device may be used to track the gaze direction of each eye (e.g., based on tracking a patient's pupils) may also be used to determine the binocular horizontal and vertical alignment of each eye independently as well as for measuring the patient's distance and near phorias. A phoria may be a misalignment of an eyes so that its natural resting point is not perfectly aligned. It may only be discovered when one eye is covered or when the two eyes are looking at different targets. In some embodiments, the image on the display screen may be converted into holographic images that are shown independently to each eye viewing the image through the first computing device. These images may be alternated to simulate one eye being covered up for determining phorias.

As stated above, a distance that the patient is located from the first computing device may be determined using a combination of the first and second computing devices. In some embodiments, the first computing device comprises a camera and determining a distance that the patient is located from the second computing device may be based on the first computing device being pointed to a computer monitor frame associated with the second computing device. As a patient walks away from the computer monitor frame, the first computing device may indicate by either visual indicator or an auditory sound that the patient has reached a predetermined distance from the second computing device. This indication may be based on entering a size of the computer monitor frame of the second computing device (e.g., 21") or having the first computing device automatically determine a size of the computer monitor frame. As a patient walks away from the computer monitor frame, the first computing device may determine, based on viewing the computer monitor frame, a distance that a patient should be from the computer monitor frame. Thus, the camera and an onboard processor may calculate a determined distance away from the computer monitor frame based on a known size of the computer monitor frame and this information may be transmitted to the second computing device which may use this information to determine when the patient is at a proper distance to be tested. Thus, the second computing device may be paired to the first computing device to measure precise distances from the second computing device for independently determining the position of the first eye and the second eye at all times while the first computing device is worn.

In some embodiments, the first computing device comprises an augmented reality laser pointer that is pointed to the computer monitor frame of the second computing device. In some embodiments, a camera in the first computing device may be used for determining a distance using augmented reality. As a patient walks away from the computer monitor frame, the augmented reality laser pointer, or camera, may indicate by either visual indicator or an auditory sound that the patient has reached a predetermined distance from the first computing device. This indication may be based on the augmented reality laser pointer, or camera, determining a time it takes the laser to reach a display screen associated with the first computing device. As a patient walks away from the display screen, the second computing device may determine, based on the augmented reality laser pointer, or camera, a distance that a patient should be from the computer monitor frame and the first computing device may use this information to determine when the patient is at a proper distance to be tested.

In some embodiments, a circular augmented reality fence may be utilized. A radius of the fence may be at a predetermined distance from the first computing device. For example, the radius may be 10 feet and thus the binocular alignment calculation may function as long as the patient is within a 10 foot from the first computing device (or a display screen associated with the first computing device). As a patient aims the augmented reality laser pointer, or camera, at the display screen associated with the first computing device, the second computing device may display a first color (e.g., red) until the patient reaches a correct distance (e.g., 10 ft) and, in this case, the screen associated with the second computing device may change to a second color (e.g., green). This change in color may indicate to a patient that they are at a proper distance and can take the visual acuity test. Also, in some embodiments, when the change in color occurs, a message may be sent to the first computing that indicates that a patient is at the defined distance.

In some embodiments, the first computing device marks a location of the second computing device when the first computing device is within close proximity to the second computing device. This may be performed by capturing one or more coordinates associated with the second computing device. The coordinates may be, for example, GPS coordinates so the GPS location of the second computing device is known. This marking may also capture a signal strength of a WIFI router to determine a distance from the router. The patient may then move away from the second computing device and be notified by either visual indicator or an auditory sound that the patient has reached a predetermined distance from the second computing device based on new coordinates determined by the second computing device and/or a signal strength of the WIFI router.

For example, distance may be based on a combination of using round-trip time (RTT) such as Wi-Fi RTT, GPS dual-frequency and carrier phase measurements. Wi-Fi RTT ranging and indoor position estimation may be based on making measurements of the time of flight of RF signals, and may be used to accurately estimate an indoor position of the patient.

Once a patient is at a predetermined real distance from the first computing device, at 240, the binocular alignment procedure may begin and the binocular alignment may be calculated at the second computing device based on a ratio utilizing the distance and near phorias.

The first computing device may be paired to the second computing device to measure precise distances from the first computing device for independently determining the position of the first eye and the second eye at all times while the first computing device is worn. In some embodiments, the gaze direction of the first eye and the gaze direction of the second eye may be between 18 and 22 feet for distance vision and between 16-24 inches for near vision. Thus, the distance between the first computing device and the second device may be tracked for feet as well as inches. In some embodiments, a binocular alignment calculation may be based on the patient in their natural state, wherein natural state comprises standing, sitting, reading, viewing a PC or wearing an augmented reality headset. In other words, the calculation is not based on the patient being in a single position that is used for measuring binocular alignment calculations.

Figure 3:
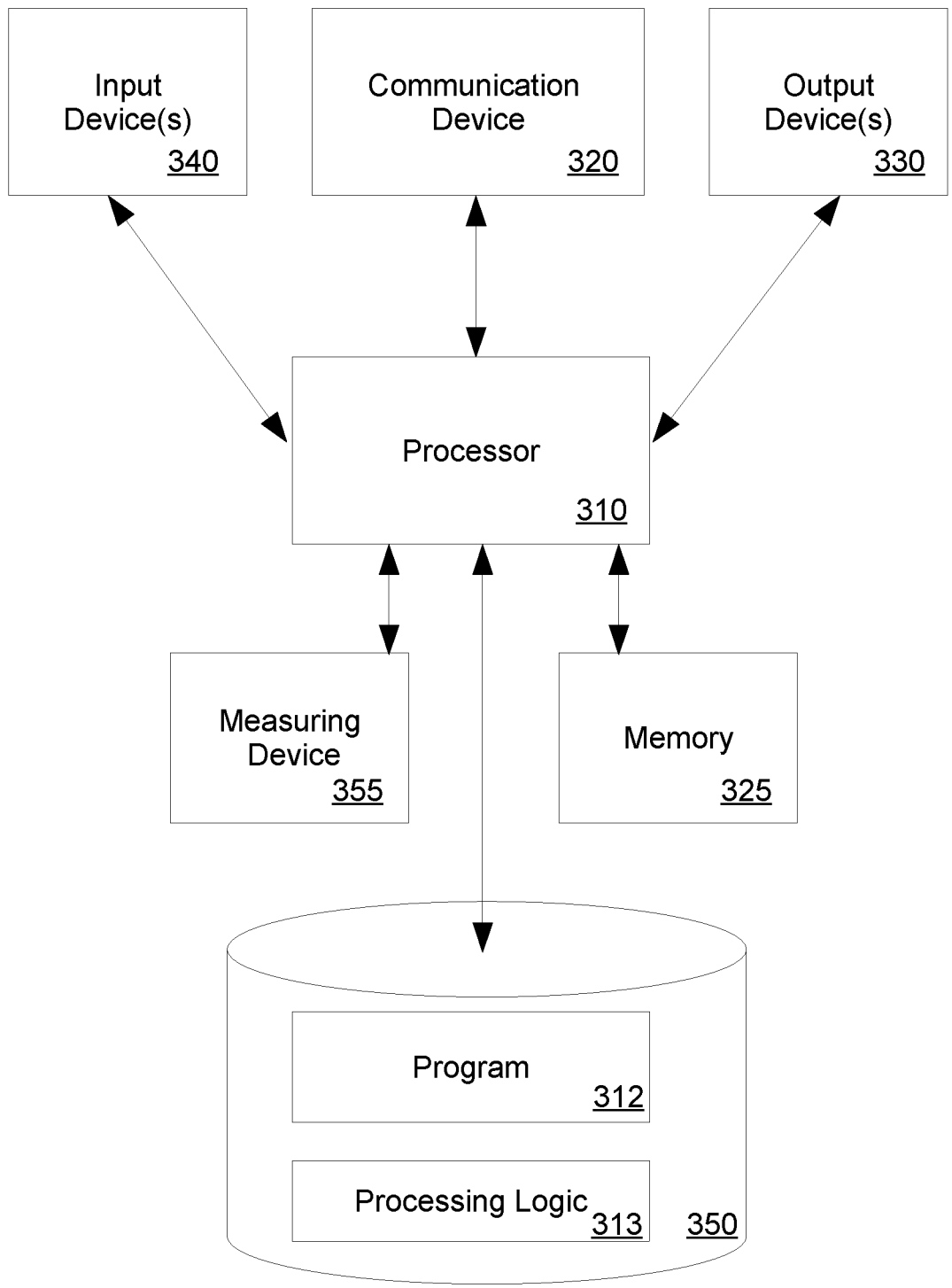
FIG. 3 illustrates a remote device in accordance with some embodiments.

Note the embodiments described herein may be implemented using any number of different hardware configurations. For example, FIG. 3 illustrates a mobile device 300 that may be, for example, associated with the visual acuity system 100 of FIG. 1. The mobile device 300 may provide a technical and commercial advantage by being able to determine a distance a patient is away from a display screen so that a safe binocular alignment calculation may be performed at home.

The mobile device 300 may comprise a processor 310 ("processor"), such as one or more commercially available Central Processing Units (CPUs) in the form of one-chip microprocessors, coupled to a communication device 320 configured to communicate via a communication network (not shown in FIG. 3). The communication device 320 may be used to communicate, for example, with one or more machines on a network. The mobile device 300 further includes an input device 340 (e.g., a mouse and/or keyboard to enter answers to a visual acuity test) and an output device 330 (e.g., to output and display the data and/or alerts). The output device 330 may comprise a screen that utilizes augmented reality technology for displaying target/images that vary in size, detail (pixels) and retinal disparity. The target/images displayed may be holographic in nature. The mobile device 300 may further comprise a measuring device 355. The measuring device 355 may comprise a GPS radio, a camera, a radio transceiver and/or an augmented reality laser pointer.

The processor 310 also communicates with a memory 325 and storage device 350 that stores data 313. The storage device 350 may comprise any appropriate information storage device, including combinations of magnetic storage devices (e.g., a hard disk drive), optical storage devices, mobile telephones, and/or semiconductor memory devices. The storage device 350 may store a program 312 and/or processing logic 313 for controlling the processor 310. The processor 310 performs instructions of the programs 312, 313, and thereby operates in accordance with any of the embodiments described herein. For example, the processor 310 may receive distance data may institute an alert to a patient via the instructions of the programs 312 and processing logic 313.

The programs 312, 313 may be stored in a compiled, compressed, uncompiled and/or encrypted format or a combination. The programs 312, 313 may furthermore include other program elements, such as an operating system, a database management system, and/or device drivers used by the processor 310 to interface with peripheral devices.

As will be appreciated by one skilled in the art, the present embodiments may be embodied as a system, method or computer program product. Accordingly, the embodiments described herein may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the embodiments described herein may take the form of a computer program product embodied in one or more computer readable medium(s) having computer readable program code embodied thereon.

The process flow and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein. The method steps can then be carried out using the distinct software modules and/or sub-modules of the system, as described above, executing on one or more hardware processors. Further, a computer program product can include a computer-readable storage medium with code adapted to be implemented to carry out one or more method steps described herein, including the provision of the system with the distinct software modules.

This written description uses examples to disclose multiple embodiments, including the preferred embodiments, and also to enable any person skilled in the art to practice the invention, including making and using any devices or systems and performing any incorporated methods. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

What is claimed:

1. A system for calculating binocular alignment, the system comprising:
   a second computing device to determine a position of a first eye and a second eye; and
   a first computing device to display different images at real distances from the second computing device for a first eye associated with a patient and a second eye associated with the patient, where the first computing device is worn by the patient wherein the first computing device tracks a gaze direction of the first eye and a gaze direction of the second eye to determine a binocular horizontal, pure symmetric vergence along the patient's egocentric midline while one or more targets are displaced in depth at real physical distances from a monitor associated with the second computing device or by using augmented reality.

2. The system for calculating binocular alignment of claim 1, wherein the first computing device is paired to the second computing device to measure precise distances from the first computing device for independently determining the position of the first eye and the second eye at all times while the first computing device is worn.

3. The system for calculating binocular alignment of claim 2, wherein the first computing device tracks a gaze direction of the first eye and a gaze direction of the second eye to determine the binocular horizontal and vertical alignment of each eye independently and measures the patient's distance and near phorias.

4. The system for calculating binocular alignment of claim 3, wherein binocular alignment is calculated by the second computing device based on a ratio utilizing the distance and near phorias.

5. The system for calculating binocular alignment of claim 4, wherein binocular alignment is based on the patient in their natural state, wherein natural state comprises standing, sitting, reading, viewing a PC or wearing an augmented reality headset.

6. The system for calculating binocular alignment of claim 1, wherein the first computing device is an augmented reality headset.

7. The system for calculating binocular alignment of claim 1 wherein the gaze direction of the first eye and the gaze direction of the second eye is between 18 and 22 feet for distance vision and between 16-24 inches for near vision.

8. A method of calculating binocular alignment, the method comprising:
   initiating a binocular alignment test on a first computing device;
   linking a program on a second computing device with the binocular alignment test on the first computing device;
   tracking, at real distances from the first computing device to the second computing device, a gaze direction of a first eye of a patient and a gaze direction of a second eye of a patient to determine (i) a binocular horizontal, pure symmetric vergence along the patient's egocentric midline while one or more targets are displaced in depth at real physical distances by using augmented reality, (ii) the binocular horizontal and vertical alignment of each eye independently and (iii) to measures the patient's distance and near phorias; and
   calculating the binocular alignment at the second computing device based on a ratio utilizing the distance and near phorias wherein the gaze direction of the first eye and the gaze direction of the second eye is between 18 and 22 feet for distance vision and between 16-24 inches for near vision.

9. A non-transitory computer-readable medium comprising processor steps that when executed by a processor perform a method of calculating binocular alignment, the method comprising:
   initiating a binocular alignment test on a first computing device;
   linking a program on a second computing device with the binocular alignment test on the first computing device;
   tracking, at real distances from the first computing device to the second computing device, a gaze direction of a first eye of a patient and a gaze direction of a second eye of a patient to determine (i) a binocular horizontal, pure symmetric vergence along the patient's egocentric midline while one or more targets are displaced in depth at real physical distances by using augmented reality, (ii) the binocular horizontal and vertical alignment of each eye independently and (iii) to measures the patient's distance and near phorias; and
   calculating the binocular alignment at the second computing device based on a ratio utilizing the distance and near phorias wherein the gaze direction of the first eye and the gaze direction of the second eye is between 18 and 22 feet for distance vision and between 16-24 inches for near vision.

* * * * *